(12) United States Patent
Nathan

(10) Patent No.: US 6,866,860 B2
(45) Date of Patent: Mar. 15, 2005

(54) CATIONIC ALKYD POLYESTERS FOR MEDICAL APPLICATIONS

(75) Inventor: Aruna Nathan, Bridgewater, NJ (US)

(73) Assignee: Ethicon, Inc., Somerville, NJ (US)

( * ) Notice: Subject to any disclaimer, the term of this patent is extended or adjusted under 35 U.S.C. 154(b) by 28 days.

(21) Appl. No.: 10/323,367

(22) Filed: Dec. 19, 2002

(65) Prior Publication Data

US 2004/0120980 A1 Jun. 24, 2004

(51) Int. Cl.$^7$ ............... A61F 2/00; B32B 7/02; A61K 31/70
(52) U.S. Cl. ............... 424/426; 528/291; 528/295.5; 528/302; 528/306; 528/335; 528/354; 528/361; 525/437; 525/439; 525/440; 525/444; 525/445; 525/447; 525/448; 525/450; 428/221; 428/304.4; 428/308.4; 428/402; 428/480; 424/424; 424/444; 424/445; 424/447; 424/457; 514/23; 514/54; 514/772.3; 514/772.6; 514/778; 514/802; 514/816; 524/801; 524/804
(58) Field of Search ............... 528/291, 295.5, 528/302, 306, 335, 354, 361; 525/437, 439, 440, 444, 445, 447, 448, 450; 428/221, 304.4, 308.4, 402, 480; 424/424, 426, 444, 445, 447, 457; 514/23, 54, 772.3, 772.6, 778, 802, 816; 524/604, 801

(56) References Cited

U.S. PATENT DOCUMENTS

| | | |
|---|---|---|
| 2,895,930 A | 7/1959 | Milton |
| 3,278,464 A | 10/1966 | Boyer et al. |
| 3,808,479 A | 4/1974 | Cunningham et al. |
| 3,978,203 A | 8/1976 | Wise |
| 3,997,512 A | 12/1976 | Casey et al. |
| 4,048,256 A | 9/1977 | Casey et al. |
| 4,076,798 A | 2/1978 | Casey et al. |
| 4,095,600 A | 6/1978 | Casey et al. |
| 4,118,470 A | 10/1978 | Casey et al. |
| 4,122,129 A | 10/1978 | Casey et al. |
| 4,163,073 A | 7/1979 | Pepe et al. |
| 4,384,975 A | 5/1983 | Fong |
| 4,419,139 A | 12/1983 | Gooch et al. |
| 4,568,559 A | 2/1986 | Nuwayser et al. |
| 5,137,743 A | 8/1992 | Zaks et al. |
| 5,155,246 A | 10/1992 | Naskar et al. |
| 5,219,980 A | 6/1993 | Swidler |
| 5,306,311 A | 4/1994 | Stone et al. |
| 5,308,623 A | 5/1994 | Fues et al. |
| 5,360,626 A | 11/1994 | Iyengar et al. |
| 5,411,554 A | 5/1995 | Scopelianos et al. |
| 5,442,033 A | 8/1995 | Bezwada |
| 5,464,929 A | 11/1995 | Bezwada et al. |
| 5,525,646 A | 6/1996 | Lundgren et al. |
| 5,599,852 A | 2/1997 | Scopelianos et al. |
| 5,607,687 A | 3/1997 | Bezwada et al. |
| 5,728,752 A | 3/1997 | Scopelianos et al. |
| 5,618,552 A | 4/1997 | Bezwada et al. |
| 5,628,993 A | 5/1997 | Yamagata et al. |
| 5,631,015 A | 5/1997 | Bezwada et al. |
| 5,653,992 A | 8/1997 | Bezwada et al. |
| 5,670,478 A | 9/1997 | Stuchlik et al. |
| 5,698,213 A | 12/1997 | Jamiolkowski et al. |
| 5,700,583 A | 12/1997 | Jamiolkowski et al. |
| 5,725,881 A | 3/1998 | Buchholz et al. |
| 5,750,100 A | 5/1998 | Yamagata et al. |
| 5,753,234 A | 5/1998 | Lee et al. |
| 5,824,333 A | 10/1998 | Scopelianos et al. |
| 5,859,150 A | 1/1999 | Jamiolkowski et al. |
| 5,998,552 A | 12/1999 | Gruber et al. |
| 6,074,660 A | 6/2000 | Jamiolkowski et al. |
| 6,100,346 A | 8/2000 | Jamiolkowski et al. |
| 6,110,501 A | 8/2000 | Redding, Jr. et al. |
| 6,114,458 A | 9/2000 | Hawker et al. |
| 6,120,787 A | 9/2000 | Gustafsson et al. |
| 6,121,398 A | 9/2000 | Wool et al. |
| 6,147,168 A | 11/2000 | Jamiolkowski et al. |
| 6,224,894 B1 | 5/2001 | Jamiolkowski et al. |
| 6,251,435 B1 | 6/2001 | Jamiolkowski et al. |
| 6,268,329 B1 | 7/2001 | Markussen |
| 6,335,383 B1 | 1/2002 | Scopelianos et al. |
| 2001/0007771 A1 | 7/2001 | Sullivan et al. |
| 2002/0037301 A1 | 3/2002 | De La Poterie |
| 2003/0185752 A1 | 10/2003 | Nathan et al. |

FOREIGN PATENT DOCUMENTS

| | | |
|---|---|---|
| DE | 1694845 A | 8/1971 |
| EP | 0422209 B1 | 3/1995 |
| EP | 841361 A1 | 5/1995 |
| EP | 747072 A | 12/1996 |
| EP | 1270024 A | 1/2003 |
| EP | 1348451 A | 10/2003 |
| EP | 1369136 A | 12/2003 |
| EP | 1374860 A | 1/2004 |
| GB | 630924 A | 10/1949 |
| WO | WO 88/03785 A1 | 6/1988 |
| WO | WO 89/08694 A1 | 9/1989 |
| WO | WO 90/12604 A1 | 11/1990 |
| WO | WO 92/12645 | 8/1992 |
| WO | WO 93/08850 A1 | 5/1993 |
| WO | WO 94/25079 A1 | 11/1994 |
| WO | WO 94/15079 A1 | 11/1995 |
| WO | WO 95/33821 A1 | 12/1995 |
| WO | WO 97/09367 | 3/1997 |
| WO | WO 97/23608 A1 | 7/1997 |

(List continued on next page.)

OTHER PUBLICATIONS

Brian Parkyn F. Lamb and B. V. Clifton, "Polyesters vol. 2 Unsaturated Polyesters and Polyester Plasticisers," London Iliffe Books Ltd., New York American Elsevier ublishing Company, Inc., 1967 pp. 107–122.

(List continued on next page.)

Primary Examiner—Samuel A. Acquah

(57) ABSTRACT

The present invention is directed to medical devices or pharmaceutical composition, each containing a synthetic, biodegradable, biocompatible polymer that is the reaction product of a polybasic acid or derivative thereof, a monoglyceride, and a cationic polyol.

38 Claims, No Drawings

FOREIGN PATENT DOCUMENTS

| WO | WO 99/29303 A1 | 6/1999 |
| WO | WO 99/29758 A1 | 6/1999 |
| WO | WO 00/02950 A1 | 1/2000 |
| WO | WO 00/35511 A | 6/2000 |
| WO | WO 01/07485 A1 | 2/2001 |
| WO | WO 01/07488 A1 | 2/2001 |
| WO | WO 01/76649 A | 10/2001 |

OTHER PUBLICATIONS

Temple C. Patton, "Alkyd Resin Technology—Formulating Techniques and Allied Calculations," Interscience Publishers, a of John Wiley and Sons, New York–London 1962, pp. 13–31.

EPO Search Reports dated Apr. 22, 2004, Apr. 23, 2004, another Apr. 23, 2004, & Apr. 28, 2004.

Database WPI Week 199430 Derwent Publications LTD., London, GB; an 1994–248859 XP002256761 & WO 94 15581 A. (Hisamitau), Jul. 12, 1994 abstract.

Mark H.F.; "Alkyd Resins ", Encyclodpedia of Polmer Sience and Engineering. A to Amorphous Polymers, New York, J. Wiley & Sons, US. vol. 1, pp. 644–648 xP002035651 "the whole document".

Emiko Koyama, Fumio Sanda, and Takeshi Endo, "Synthesis of Poly(ester–amide)s Derived from Optically Active Amino Alcohols, " Macromol. Symp., 122, 275–280 (1997).

Emiko Koyma, Fumio Sanda, and Takeshi Endo, "Polycondensations of Hydroxycarboxylic Acids Derived from Optically Active Aminosicohols and Acid Anhydrides —Synthesis of Funtional Poly(ester–amid)s, " Journal of Polymar Science: Part A: Polymr Chemistry 35, 345–352 (1997).

Donald L. Elbert, Alison B. Pratt, Matthias P. Lutolf, Sven Halstenberg, Jeffery A. Hubbell, "Protein Delivery from Materials Formed by Self–selective Conjugsis Addition Reactions," Journal of Controlled Release, 76, 11–25 (2001).

EPO Search Report dated Dec. 15, 2003 for EPO Appl. No. EP 03 25 1999.

CATIONIC ALKYD POLYESTERS FOR MEDICAL APPLICATIONS

FIELD OF THE INVENTION

The present invention relates to biodegradable and biocompatible polymers for use in pharmaceutical and medical applications.

BACKGROUND OF THE INVENTION

Both natural and synthetic polymers, including homopolymers and copolymers, which are both biocompatible and degradable in vivo are known for use in the manufacture of medical devices that are implanted in body tissue and degrade over time. Examples of such medical devices include suture anchor devices, sutures, staples, surgical tacks, clips, plates, screws, drug delivery devices, adhesion prevention films and foams, and tissue adhesives.

Natural polymers may include catgut, cellulose derivatives and collagen. Natural polymers typically degrade by an enzymatic degradation process in the body.

Synthetic polymers may include aliphatic polyesters, polyanhydrides and poly(orthoester)s. Synthetic degradable polymers typically degrade by a hydrolytic mechanism. Such synthetic degradable polymers include homopolymers, such as poly(glycolide), poly(lactide), poly(e-caprolactone), poly(trimethylene carbonate) and poly(p-dioxanone), and copolymers, such as poly(lactide-co-glycolide), poly(e-caprolactone-co-glycolide), poly(glycolide-co-trimethylene carbonate), poly(alkylene diglycolate), and polyoxaesters. The polymers may be statistically random copolymers, segmented copolymers, block copolymers or graft copolymers.

Alkyd-type polyesters prepared by the polycondensation of a polyol, polyacid and fatty acid are used in the coating industry in a variety of products, including chemical resins, enamels, varnishes and paints. These polyesters also are used in the food industry to make texturized oils and emulsions for use as fat substitutes.

There is a great need for polymers for use in drug delivery and medical devices, where the polymers have both low melting temperatures and low viscosities upon melting, thus permitting for solvent-free processing techniques in preparation of medical devices and compositions, can crystallize rapidly, and biodegrade within 6 months. There is also a need for cationic polymers that are useful for the delivery of bioactive agents such as DNA, RNA, oligonucleotides, proteins, peptides, and drugs to individuals in need thereof.

SUMMARY OF THE INVENTION

The present invention is directed to medical devices and pharmaceutical compositions, each comprising a synthetic, biodegradable, biocompatible polymer comprising the reaction product of a polybasic acid or derivative thereof, a monoglyceride, and a cationic polyol.

DESCRIPTION OF THE INVENTION

Alkyd polymers have been prepared by several known methods. For example, alkyd-type polymers were prepared by Van Bemmelen (*J. Prakt. Chem.*, 69 (1856) 84) by condensing succinic anhydride with glycerol. In the "Fatty Acid" method (see Parkyn, et al. *Polyesters* (1967), Iliffe Books, London, Vol. 2 and Patton, In: *Alkyd Resins Technology*, Wiley-Interscience New York (1962)), a fatty acid, a polyol and an anhydride are mixed together and allowed to react. The "Fatty Acid-Monoglyceride" method includes a first step of esterifying the fatty acid with glycerol and, when the first reaction is complete, adding an acid anhydride. The reaction mixture then is heated and the polymerization reaction takes place. In the "Oil-Monoglyceride" method, an oil is reacted with glycerol to form a mixture of mono-, di-, and triglycerides. This mixture then is polymerized by reacting with an acid anhydride.

The synthetic, biodegradable, biocompatible polymers utilized in the present invention are the reaction product of a polybasic acid or derivative thereof, a monoglyceride, and a cationic polyol and may be classified as cationic alkyd polyesters. Preferably, the polymers of the present invention are prepared by the polycondensation of a polybasic acid or derivative thereof, a monoglyceride, wherein the monoglyceride comprises reactive hydroxy groups and fatty acid groups, and a cationic polyol. The expected hydrolysis byproducts are glycerol, a cationic polyol, dicarboxylic acid(s), and fatty acid(s), all of which are biocompatible. The polymers comprise an aliphatic polyester backbone with pendant fatty acid ester groups. Long chain saturated fatty acids result in polymers that are polymeric waxes that crystallize rapidly and exhibit relatively low melting points, e.g. between about 25° C. and 70° C. As used herein, a wax is a solid, low-melting substance that is plastic when warm and, due to its relatively low molecular weight, is fluid when melted. Alternatively, use of unsaturated fatty acids or short chain fatty acids results in liquid polymers. As used herein, a liquid polymer is a polymer that is liquid at room temperature, with a melt temperature of less than about 25° C. preferably less than about 20° C.

The polymeric waxes and liquid polymers can be blended to form injectable microdispersions. The microdispersions can be formed by physically blending liquid polymers of the present invention with finely ground polymeric waxes of the present invention, or by grinding a suspension of large pieces of the polymeric wax using the liquid polymer as a lubricant, until the desired particle size distribution is obtained.

Generally, the polymeric wax will have an average particle diameter of less than about 500 microns and preferably less than 50 microns. It is currently preferred to mix the finely ground polymeric wax and liquid polymer and raise the temperature of the mixture to a temperature sufficient to melt the polymeric wax (melt blending). Melt blending is preferred because it simplifies the mixing operation involved in producing the microdispersion. It is desirable to avoid excessive heating during melt blending to avoid transesterification of the polymers.

Monoglycerides that may be used to prepare the polymers utilized in the present invention include, without limitation, monostearoyl glycerol, monopalmitoyl glycerol, monomyrisitoyl glycerol, monocaproyl glycerol, monodecanoyl glycerol, monolauroyl glycerol, monolinoleoyl glycerol, monooleoyl glycerol, and combinations thereof. Preferred monoglycerides include monostearoyl glycerol, monopalmitoyl glycerol and monomyrisitoyl glycerol.

Polybasic acids that can be used include natural multifunctional carboxylic acids, such as succinic, glutaric, adipic, pimelic, suberic, and sebacic acids; hydroxy acids, such as diglycolic, malic, tartaric and citric acids; and unsaturated acids, such as fumaric and maleic acids. Polybasic acid derivatives include anhydrides, such as succinic anhydride, diglycolic anhydride, glutaric anhydride and maleic anhydride, mixed anhydrides, esters, activated esters and acid halides. The multifunctional carboxylic acids listed above are preferred.

Cationic polyols that can be used include polyols and diols containing amine groups. Preferable diols include tertiary amine-containing diols such as N-methyl diethanolamine and 3-dimethylamino-1,2 propanediol.

In preparing the polymers utilized in the present invention, the particular chemical and mechanical properties required of the polymer for a particular use must be considered. For example, changing the chemical composition can vary the physical and mechanical properties, including absorption times. Copolymers can be prepared by using mixtures of diacids, different monoalkanoyl glycerides and different cationic polyols to match a desired set of properties. Similarly, blends of two or more cationic alkyd polyesters may be prepared to tailor properties for different applications.

Multifunctional monomers may be used to produce crosslinked polymeric networks. Alternatively, double bonds may be introduced by using monoglycerides or diacids containing at least one double bond to allow photo-crosslinking. Hydrogels may be prepared using this approach provided the polymer is sufficiently water soluble or swellable.

Functionalized polymers can be prepared by appropriate choice of monomers. Polymers having pendant hydroxyls can be synthesized using a hydroxy acid such as malic or tartaric acid in the synthesis. Polymers with pendent amines, carboxyls or other functional groups also may be synthesized.

A variety of biological active substances, hereinafter referred to as bioactive agents, can be covalently attached to these functional polymers by known coupling chemistry to give sustained release of the bioactive agent. As used herein, bioactive agent is meant to include those substances or materials that have a therapeutic effect on mammals, e.g. pharmaceutical compounds.

In another embodiment, the polymers of the present invention may be endcapped in a variety of ways to obtain the desired properties. Endcapping reactions convert the terminal and pendant hydroxyl groups and terminal carboxyl groups into other types of chemical moieties. Typical endcapping reactions include but are not limited to alkylation and acylation reactions using common reagents such as alkyl, alkenyl, or alkynyl halides and sulfonates, acid chlorides, anhydrides, mixed anhydrides, alkyl and aryl isocyanates and alkyl and aryl isothiocyanates. Endcapping reactions can impart new functionality to the polymers of this invention. For instance, when acryloyl or methacryloyl chloride is used to endcap these polymers, acrylate or methacrylate ester groups, respectively, are created that subsequently can be polymerized to form a crosslinked network. One skilled in the art, once having the benefit of the disclosure herein, will be able to ascertain particular properties of the liquid polymers required for particular purposes and readily prepare liquid polymers that provide such properties.

The polymerization of the cationic alkyd polyesters preferably is performed under melt polycondensation conditions in the presence of an organometallic catalyst at elevated temperatures. The organometallic catalyst preferably is a tin-based catalyst, e.g. stannous octoate. The catalyst preferably will be present in the mixture at a mole ratio of polyol and polycarboxylic acid to catalyst in the range of from about 15,000/1 to 80,000/1. The reaction preferably is performed at a temperature no less than about 120° C. Higher polymerization temperatures may lead to further increases in the molecular weight of the copolymer, which may be desirable for numerous applications. The exact reaction conditions chosen will depend on numerous factors, including the properties of the polymer desired, the viscosity of the reaction mixture, and melting temperature of the polymer. The preferred reaction conditions of temperature, time and pressure can be readily determined by assessing these and other factors.

Generally, the reaction mixture will be maintained at about 150° C. The polymerization reaction can be allowed to proceed at this temperature until the desired molecular weight and percent conversion is achieved for the copolymer, which typically will take from about 15 minutes to 24 hours. Increasing the reaction temperature generally decreases the reaction time needed to achieve a particular molecular weight.

In another embodiment, copolymers of cationic alkyd polyesters can be prepared by forming a cationic alkyd polyester prepolymer polymerized under melt polycondensation conditions, then adding at least one aliphatic polyester monomer or aliphatic polyester prepolymer. The mixture then would be subjected to the desired conditions of temperature and time to copolymerize the prepolymer with the aliphatic polyester monomers. The aliphatic polyester monomers for this embodiment can be selected from the group consisting of glycolide, L-lactide, D-lactide, meso-lactide, rac-lactide, $\epsilon$-caprolactone, trimethylene carbonate, p-dioxanone, 1,4-dioxanone, 1,4-dioxepan-2-one, 1,5-dioxepan-2-one and substituted derivatives thereof.

The molecular weight of the prepolymer, as well as its composition, can be varied depending on the desired characteristic that the prepolymer is to impart to the copolymer. Those skilled in the art will recognize that the cationic alkyd polyester prepolymers described herein can also be made from mixtures of more than one monoglyceride, dioxycarboxylic acid, or cationic polyol.

The polymers, copolymers and blends of the present invention can be crosslinked to affect mechanical properties. Crosslinking can be accomplished by the addition of crosslinking enhancers, irradiation, e.g. gamma-irradiation, or a combination of both. In particular, crosslinking can be used to control the amount of swelling that the materials of this invention experience in water.

One of the beneficial properties of the cationic alkyd polyesters of this invention is that the ester linkages in the alkyd block are hydrolytically unstable and, therefore, the polymer is biodegradable because it readily breaks down into small segments when exposed to moist body tissue. In this regard, while it is envisioned that co-reactants could be incorporated into the reaction mixture of the polybasic acid, the monoglyceride and the cationic polyol for the formation of the cationic alkyd polyesters, it is preferable that the reaction mixture does not contain a concentration of any co-reactant which would render the subsequently prepared polymer nondegradable. Preferably, the reaction mixture is substantially free of any such co-reactants if the resulting polymer is rendered nondegradable.

In one embodiment of the invention, the cationic alkyd polyesters of the present invention can be used as a pharmaceutical carrier in a drug delivery matrix. Solid cationic alkyd polyester waxes could be used to coat or encapsulate a bioactive agent. Alternatively, an effective amount of a bioactive agent could be mixed with injectable microdispersions of polymeric wax and liquid polymer. Such a microdispersion would be particularly suitable for unstable drugs such as proteins.

The variety of bioactive agents that can be used in conjunction with the polymers of the invention is vast. In general, bioactive agents which may be administered via pharmaceutical compositions of the invention include, without limitation, antiinfectives, such as antibiotics and antiviral agents; analgesics and analgesic combinations; anorexics; antihelmintics; antiarthritics; antiasthimatic agents; anticonvulsants; antidepressants; antidiuretic agents; antidiarrheals; antihistamines; antiinflammatory agents; antimigraine preparations; antinauseants; antineoplastics; antiparkinsonism drugs; antipruritics; antipsychotics; antipyretics; antispasmodics; anticholinergics; sympathomimetics; xanthine derivatives; cardiovascular preparations including calcium channel blockers and beta-blockers such as pindolol and antiarrhythmics; antihypertensives; diuretics; vasodilators, including general coronary, peripheral and cerebral; central nervous system stimulants; cough and cold preparations, including decongestants; hormones, such as estradiol and other steroids, including corticosteroids; hypnotics; immunosuppressives; muscle relaxants; parasympatholytics; psychostimulants; sedatives; tranquilizers; naturally derived or genetically engineered proteins, growth factors, polysaccharides, glycoproteins or lipoproteins; oligonucleotides; antibodies; antigens; cholinergics; chemotherapeutics; hemostatics; clot dissolving agents; radioactive agents; and cystoslatics.

Rapamycin, risperidone, and erythropoietin are several bioactive agents that may be used in drug delivery matrices of the present invention.

The drug delivery matrix may be administered in any suitable dosage form such as oral, parenteral, pulmonary, buccal, nasal, ocular, topical, vaginal routes, or as a suppository. Bioerodible particles, ointments, gels, creams, and similar soft dosage forms adapted for the administration via the above routes may also be formulated. Other modes of administration, e.g. transdermal, and compositional forms, e.g. more rigid transdermal forms, are within the scope of the invention as well.

Parenteral administration of a bioerodible composition of the invention can be effected by either subcutaneous or intramuscular injection. The bioactive agent could be encapsulated in particles made of the solid polymer. Alternatively, parenteral formulations of the copolymer may be formulated by mixing one or more pharmaceuticals with a liquid copolymer or microdispersion. Other suitable parenteral additives may be formulated with the copolymer and pharmaceutical active. However, if water is to be used it should be added immediately before administration. Bioerodible ointment, gel or cream may also be injected as is or in combination with one or more suitable auxiliary components as described below. Parenteral delivery is preferred for administration of proteinaceous drugs such as growth factors, growth hormone, or the like.

The bioerodible ointments, gels and creams of the invention will include an ointment, gel or cream base comprising one or more of the copolymers described herein and a selected bioactive agent. The bioactive agent, whether present as a liquid, a finely divided solid, or any other physical form, is dispersed in the ointment, gel or cream base. Typically, but optionally, the compositions include one or more other components, e.g., nontoxic auxiliary substances such as colorants, diluents, odorants, carriers, excipients, stabilizers or the like.

The quantity and type of copolymers incorporated into the parenteral, ointment, gel, cream, etc., is variable. For a more viscous composition, a higher molecular weight polymer is used. If a less viscous composition is desired, a lower molecular weight polymer can be employed. The product may contain blends of the liquid or low melting point copolymers to provide the desired release profile or consistency to a given formulation.

While not essential for topical or transdermal administration of many drugs, in some cases, it may be preferred that a skin permeation enhancer be coadministered with the drug. Any number of the many skin permeation enhancers known in the art may be used. Examples of suitable enhancers include dimethylsulfoxide (DMSO), dimethylformamide (DMF), N,N-dimethylacetamide (DMA), deslymethylsulfoxide, ethanol, eucalyptol, lecithin, and the 1-N-dodecylcyclazacycloheptan-2-ones.

Depending on dosage form, the pharmaceutical compositions of the present invention may be administered in different ways, i.e. parenterally, topically, or the like. Preferred dosage forms are liquid dosage forms that can be administered parenterally.

The amount of bioactive agent will be dependent upon the particular drug employed and medical condition being treated. Typically, the amount of drug represents about 0.001% to about 70%, more typically about 0.001% to about 50%, most typically about 0.001% to about 20% by weight of the matrix.

The quantity and type of cationic alkyd polyester incorporated into the parenteral will vary depending on the release profile desired and the amount of drug employed. The product may contain blends of polymers to provide the desired release profile or consistency to a given formulation.

The cationic alkyd polyester, upon contact with body fluids, including blood or the like, undergoes gradual degradation, mainly through hydrolysis, with concomitant release of the dispersed drug for a sustained or extended period, as compared to the release from an isotonic saline solution. This can result in prolonged delivery of effective amounts of drug, e.g. over about 1 to about 2,000 hours, preferably about 2 to about 800 hours, or, e.g. 0.0001 mg/kg/hour to 10 mg/kg/hour. This dosage form can be administered as is necessary, depending on the subject being treated, the severity of the affliction, the judgment of the prescribing physician, and the like.

Individual formulations of drugs and cationic alkyd polyester may be tested in appropriate in vitro and in vivo models to achieve the desired drug release profiles. For example, a drug could be formulated with a and orally administered to an animal. The drug release profile could then be monitored by appropriate means, such as by taking blood samples at specific times and assaying the samples for drug concentration. Following this or similar procedures, those skilled in the art will be able to formulate a variety of formulations.

In a further embodiment of the present invention, the polymers and blends thereof can be used in tissue engineering applications, e.g. as supports for cells or delivery vehicle for cells. Appropriate tissue scaffolding structures are known in the art, such as the prosthetic articular cartilage described in U.S. Pat. No. 5,306,311, the porous biodegradable scaffolding described in WO 94/25079, and the prevascularized implants described in WO 93/08850 (all hereby incorporated by reference herein). Methods of seeding and/or culturing cells in tissue scaffoldings are also known in the art such as those methods disclosed in EPO 422 209 B 1, WO 88/03785, WO 90/12604 and WO 95/33821, all of which are all hereby incorporated by reference herein as if set forth in their entirety.

The polymers of this invention can be melt processed by numerous methods to prepare a vast array of useful devices. These polymers can be injection or compression molded to make implantable medical and surgical devices, especially wound closure devices. The preferred wound closure devices are surgical clips, staples and sutures.

Alternatively, the cationic alkyd polyester can be extruded to prepare filaments. The filaments thus produced may be fabricated into sutures or ligatures, attached to surgical needles, packaged, and sterilized by known techniques. The polymers of the present invention may be spun as monofilament or multifilament yarn and woven or knitted to form sponges or gauze, or used in conjunction with other molded compressive structures as prosthetic devices within the body of a human or animal where it is desirable that the structure have high tensile strength and desirable levels of compliance and/or ductility. Non-woven sheets also may be prepared and used as described above. Useful embodiments include tubes, including branched tubes, for artery, vein or intestinal repair, nerve splicing, tendon splicing, sheets for taping-up and supporting damaged surface abrasions, particularly major abrasions, or areas where the skin and underlying tissues are damaged or surgically removed.

Additionally, the polymers can be molded to form films which, when sterilized, are useful as adhesion prevention barriers. Another alternative processing technique for the polymers of this invention includes solvent casting, particularly for those applications where a drug delivery matrix is desired. In more detail, the surgical and medical uses of the filaments, films, and molded articles of the present invention include, but are not limited to, knitted products, woven or non-woven, and molded products including, but not limited to burn dressings, hernia patches, meshes, medicated dressings, fascial substitutes, gauze, fabric, sheet, felt or sponge for liver hemostasis, gauze bandages, arterial graft or substitutes, bandages for skin surfaces, suture knot clip, orthopedic pins, clamps, screws, plates, clips, e.g. for vena cava, staples, hooks, buttons, snaps, bone substitutes, e.g. as mandible prosthesis, intrauterine devices, e.g. as spermicidal devices, draining or testing tubes or capillaries, surgical instruments, vascular implants or supports, e.g. stents or grafts, or combinations thereof, vertebral discs, extracorporeal tubing for kidney and heart-lung machines, artificial skin, and supports for cells in tissue engineering applications.

In another embodiment, the cationic alkyd polyester polymer is used to coat a surface of a medical device to enhance the lubricity of the coated surface. The polymer may be applied as a coating using conventional techniques. For example, the polymer may be solubilized in a dilute solution of a volatile organic solvent, such as acetone, methanol, ethyl acetate or toluene, and then the article can be immersed in the solution to coat its surface. Once the surface is coated, the surgical article can be removed from the solution where it can be dried at an elevated temperature until the solvent and any residual reactants are removed.

In another embodiment of the present invention, the solid waxes derived from cationic alkyd polyesters can be used to overcoat microparticles encapsulating a bioactive agent(s). This would help provide an additional barrier for sustained release of the drug.

The injectable microdispersions can be used for a variety of soft tissue repair and augmentation procedures. For example, the microdispersions can be used in facial tissue repair or augmentation, including but not limited to camouflaging scars, filling depressions, smoothing out irregularity, correcting asymmetry in facial hemiatrophy, second branchial arch syndrome, facial lipodystrophy and camouflaging age-related wrinkles as well as augmenting facial eminences, e.g. lips, brow, etc. Additionally, these injectable microdispersions can be used to restore or improve sphincter function, such as for treating stress urinary incontinence. Other uses of these injectable microdispersions may also include the treatment of vesicoureteral reflux (incomplete function of the inlet of the ureter in children) by subureteric injection and the application of these microdispersions as general purpose fillers in the human body.

Surgical applications for an injectable, biodegradable microdispersion include, but are not limited to, facial contouring, e.g. frown or glabellar line, acne scars, cheek depressions, vertical or perioral lip lines, marionette lines or oral commissures, worry or forehead lines, crow's feet or periorbital lines, deep smile lines or nasolabial folds, smile lines, facial scars, lips and the like; periurethral injection, including injection into the submucosa of the urethra along the urethra, at or around the urethral-bladder junction to the external sphincter, urethral injection for the prevention of urinary reflux; injection into the tissues of the gastrointestinal tract for the bulking of tissue to prevent reflux; to aid in sphincter muscle coaptation, internal or external, and for coaptation of an enlarged lumen; intraocular injection for the replacement of vitreous fluid or maintenance of intraocular pressure for retinal detachment; injection into anatomical ducts to temporarily plug the outlet to prevent reflux or infection propagation; larynx rehabilitation after surgery or atrophy; and any other soft tissue which can be augmented for cosmetic or therapeutic effect. Surgical specialists who would use such a product include, but are not limited to, plastic and reconstructive surgeons; dermatologists; facial plastic surgeons, cosmetic surgeons, otolaryngologists; urologists; gynecologists; gastroenterologists; ophthalmologists; and any other physician qualified to utilize such a product.

Additionally, to facilitate the administration and treatment of patients with the inventive microdispersion, pharmaceutically active compounds or adjuvants can be administered therewith. Pharmaceutically active agents that may be coadministered with the inventive microdispersion include but are not limited to anesthetics, e.g. lidocaine; and antiinflammatories, e.g. cortisone.

The microdispersion can be administered with a syringe and needle or a variety of devices. It is also envisioned that the microdispersion could be sold in the form of a kit comprising a device containing the microdispersion. The device having an outlet for said microdispersion, an ejector for expelling the microdispersion and a hollow tubular member fitted to the outlet for administering the microdispersion into an animal.

The dosage forms for the microdispersions of the invention are sustained-release parenterals, bioerodible ointments, gels, creams, and similar soft dosage forms.

The examples set forth below are for illustration purposes only and are not intended to limit the scope of the claimed invention in any way. Numerous additional embodiments within the scope and spirit of the invention will become readily apparent to those skilled in the art.

EXAMPLE 1

Synthesis of poly(monostearoylglyceride co succinate) solid containing 5% N-methyldiethanoamine 40.3 g (112.5 mmoles) of monostearoyl glycerol, 12.5 g (125 mmoles) of succinic anhydride and 1.5 g of N-methyldiethanoamine (12.5 mmoles) were added to a dry 100 mL, single neck, round bottom flask along with 25 μl of stannous octoate. A stir bar was added and a nitrogen inlet adapter was attached. The reaction flask was placed in a room temperature oil bath and a nitrogen blanket was started. The temperature was raised to 150° C. and maintained for 6 hours. After 6 hours, the flask was removed from the oil bath to cool to room temperature. Once the solution crystallized, it was deglassed and cleaned off any glass fragments. The polymer was a brown colored solid.

EXAMPLE 2

Synthesis of poly(monostearoylglyceride co succinate) solid containing 10% N-methyldiethanoamine 35.9 g (100 mmoles) of monostearoyl glycerol, 12.5 g (125 mmoles) of succinic anhydride and 3.0 g of N-methyldiethanoamine (25 mmoles) were added to a dry 100 mL, single neck, round bottom flask along with 25 μl of stannous octoate. A stir bar was added and a nitrogen inlet adapter was attached. The reaction flask was placed in a room temperature oil bath and a nitrogen blanket was started. The temperature was raised to 150° C. and maintained for 6 hours. After 6 hours, the flask was removed from the oil bath to cool to room temperature. Once the solution crystallized, it was deglassed and cleaned off any glass fragments. The polymer was a brown colored solid.

EXAMPLE 3

Synthesis of poly(monooleoylglyceride co succinate) liquid containing 5% N-methyldiethanoamine 40.1 g (112.5 mmoles) of monooleoyl glycerol, 12.5 g (125 mmoles) of succinic anhydride and 1.5 g of N-methyldiethanoamine (12.5 mmoles) were added to a dry 100 mL, single neck, round bottom flask along with 25 μl of stannous octoate. A stir bar was added and a nitrogen inlet adapter was attached. The reaction flask was placed in a room temperature oil bath and a nitrogen blanket was started. The temperature was raised to 150° C. and maintained for 6 hours. After 6 hours, the flask was removed from the oil bath to cool to room temperature. The polymer was a brown, transparent viscous liquid.

EXAMPLE 4

Synthesis of poly(monooleoylglyceride co succinate) liquid containing 10% N-methyldiethanoamine 36.7 g (100 mmoles) of glyceryl-monooleate, 12.5 g (125 mmoles) of succinic anhydride and 3.0 g of N-methyldiethanoamine (25 mmoles) were added to a dry 100 mL, single neck, round bottom flask along with 25 μl of stannous octoate. A stir bar was added and a nitrogen inlet adapter was attached. The reaction flask was placed in a room temperature oil bath and a nitrogen blanket was started. The temperature was raised to 150° C. and maintained for 6 hours. After 6 hours, the flask was removed from the oil bath to cool to room temperature. The polymer was a brown, transparent viscous liquid.

EXAMPLE 5

Synthesis of poly(monostearoylglyceride co succinate) solid containing 5% (3-dimethylamino-1, 2-propanediol)

40.3 g (112.5 mmoles) of monostearoyl glycerol, 12.5 g (125 mmoles) of succinic anhydride and 1.5 g of 3-dimethylamino-1,2-propanediol (12.5 mmoles) were added to a dry 100 mL, single neck, round bottom flask along with 25 μl of stannous octoate. A stir bar was added and a nitrogen inlet adapter was attached. The reaction flask was placed in a room temperature oil bath and a nitrogen blanket was started. The temperature was raised to 150° C. and maintained for 6 hours. After 6 hours, the flask was removed from the oil bath to cool to room temperature. Once the solution crystallized, it was deglassed and cleaned off any glass fragments. The polymer was a brown colored solid.

EXAMPLE 6

Synthesis of poly(monostearoylglyceride co succinate) solid containing 10% 3-dimethylamino-1,2-propanediol 35.9 g (100 mmoles) of monostearoyl glycerol, 12.5 g (125 mmoles) of succinic anhydride and 3.0 g of 3-dimethylamino-1,2-propanediol (25 mmoles) were added to a dry 100 mL, single neck, round bottom flask along with 25 μl of stannous octoate. A stir bar was added and a nitrogen inlet adapter was attached. The reaction flask was placed in a room temperature oil bath and a nitrogen blanket was started. The temperature was raised to 150° C. and maintained for 6 hours. After 6 hours, the flask was removed from the oil bath to cool to room temperature. Once the solution crystallized, it was deglassed and cleaned off any glass fragments. The polymer was a brown colored solid.

EXAMPLE 7

Synthesis of poly(monooleoylglyceride co succinate) liquid containing 5% 3-dimethylamino-1, 2-propanediol 40.1 g (112.5 mmoles) of glyceryl monooleate, 12.5 g (125 mmoles) of succinic anhydride and 1.5 g of 3-dimethylamino-1,2-propanediol (12.5 mmoles) were added to a dry 100 mL, single neck, round bottom flask along with 25 μl of stannous octoate. A stir bar was added and a nitrogen inlet adapter was attached. The reaction flask was placed in a room temperature oil bath and a nitrogen blanket was started. The temperature was raised to 150° C. and maintained for 6 hours. After 6 hours, the flask was removed from the oil bath to cool to room temperature. The polymer was a brown, transparent viscous liquid.

EXAMPLE 8

Synthesis of poly(monooleoylglyceride co succinate) liquid containing 10% 3-dimethylamino-1,2-propanediol 36.7 g (100 mmoles) of glyceryl monooleate, 12.5 g (125 mmoles) of succinic anhydride and 3.0 g of 3-dimethylamino-1,2-propanediol (25 mmoles) were added to a dry 100 mL, single neck, round bottom flask along with 25 μl of stannous octoate. A stir bar was added and a nitrogen inlet adapter was attached. The reaction flask was placed in a room temperature oil bath and a nitrogen blanket was started. The temperature was raised to 150° C. and maintained for 6 hours. After 6 hours, the flask was removed from the oil bath to cool to room temperature. The polymer was a brown, transparent viscous liquid.

I claim:

1. A medical device, comprising: a synthetic, biodegradable, biocompatible polymer comprising the reaction product of a polybasic acid or derivative thereof, a monoglyceride, and a cationic polyol.

2. The medical device of claim 1 wherein said polybasic acid or derivative thereof is selected from the group consisting of succinic acid, succinic anhydride, malic acid, tartaric acid, citric acid, diglycolic acid, diglycolic anhydride, glutaric acid, glutaric anhydride, adipic acid, pimelic acid, suberic acid, sebacic acid, fumaric acid, maleic acid, maleic anhydride, mixed anhydrides, esters, activated esters and acid halides.

3. The medical device of claim 1 wherein said monoglyceride is selected from the group consisting of monostearoyl glycerol, monopalmitoyl glycerol, monomyrisitoyl glycerol, monocaproyl glycerol, monodecanoyl glycerol, monolauroyl glycerol, monolinoleoyl glycerol and monoolcoyl glycerol.

4. The medical device of claim 3 wherein said polybasic acid derivative is succinic anhydride.

5. The medical device of claim 3 wherein said polybasic acid is succinic acid.

6. The medical device of claim 1 wherein said cationic polyol is selected from the group consisting of N-methyl diethanolamine, and 3-dimethylamino-1,2 propanediol.

7. The medical device of claim 1 wherein said polymer is branched.

8. The medical device of claim 1 wherein said polymer comprises the reaction product of said monoglyceride, said cationic polyol, and at least two of said polybasic acids or derivatives thereof selected from the group consisting of succinic acid, succinic anhydride, malic acid, tartaric acid, citric acid, diglycolic acid and diglycolic anhydride.

9. The medical device of claim 1 wherein said polymer comprises the reaction product of said polybasic acid or derivative thereof, said cationic polyol, and at least two monoglycerides selected from the group consisting of monostearoyl glycerol, monopalmitoyl glycerol, monomyrisitoyl glycerol, monocaproyl glycerol, monodecanoyl glycerol, monolauroyl glycerol, monolinoleoyl glycerol and monooleoyl glycerol.

10. The medical device of claim 1 wherein said polymer comprises the reaction product of said monoglyceride, polybasic acid or derivative thereof, N-methyl diethanolamine, and 3-dimethylamino-1,2 propanediol.

11. The medical device of claim 1 further comprising an effective amount of a bioactive agent.

12. The medical device of claim 1 further comprising end capping moieties selected from the group consisting of alkyls, alkenyls, alkynyls, acrylates, methacrylates, amines, isocyanates and isothiocyanates.

13. The medical device of claim 1 further comprising an aliphatic polyester prepared from monomers selected from the group consisting of glycolide, L-lactide, D-lactide, meso-lactide, rac-lactide, ε-caprolactone, trimethylene carbonate, p-dioxanone, 1,4-dioxanone, 1,4-dioxepan-2-one, 1,5-dioxepan-2-one and substituted derivatives thereof.

14. The medical device of claim 1 comprising a coating of said polymer.

15. The medical device of claim 14 further comprising an aliphatic polyester prepared from the group of monomers selected from the group consisting of glycolide, L-lactide, D-lactide, meso-lactide, rac-lactide, ε-caprolactone, trimethylene carbonate, p-dioxanone, 1,4-dioxanone, 1,4-dioxepan-2-one, 1,5-dioxepan-2-one and substituted derivatives thereof.

16. The medical device of claim 1 selected from the group consisting of sutures, stents, vascular grafts, stent-graft combinations, meshes, tissue engineering scaffolds, pins, clips, staples, films, sheets, foams, anchors, screws and plates.

17. The device of claim 1 wherein said polymer is a polymeric wax having a melting point between about 25° C. and about 70° C.

18. The device of claim 1 wherein said polymer is a liquid polymer having a melting point below about 25° C.

19. A composition, comprising: an effective amount of a bioactive agent, and a polymer comprising the reaction product of a polybasic acid or derivative thereof, a monoglyceride, and a cationic polyol.

20. The composition of claim 19 wherein said polybasic acid or derivative thereof is selected from the group consisting of succinic acid, succinic anhydride, malic acid, tartaric acid, citric acid, diglycolic acid, diglycolic anhydride, glutaric acid, glutaric anhydride, adipic acid, pimelic acid, suberic acid, sebacic acid and derivatives thereof.

21. The composition of claim 19 wherein said monoglyceride is selected from the group consisting of monostearoyl glycerol, monopalmitoyl glycerol, monomyrisitoyl glycerol, monocaproyl glycerol, monodecanoyl, monolauroyl glycerol, monolinoleoyl glycerol and monooleoyl glycerol.

22. The composition of claim 21 wherein said polybasic acid derivative is succinic anhydride.

23. The composition of claim 21 wherein said polybasic acid is succinic acid.

24. The composition of claim 19 wherein said polymer is branched.

25. The composition of claim 19 wherein said copolymer comprises the reaction product of said monoglyceride, said cationic polyol, and at least two of said polybasic acids or derivatives thereof selected from the group consisting of succinic acid, succinic anhydride, malic acid, tartaric acid, citric acid, diglycolic acid and diglycolic anhydride.

26. The composition of claim 19 wherein said copolymer comprises the reaction product of said polybasic acid or derivative thereof, said cationic polyol, and at least two monoglycerides selected from the group consisting of monostearoyl glycerol, monopalmitoyl glycerol, monomyrisitoyl glycerol, monocaproyl glycerol, monodecanoyl glycerol, monolauroyl glycerol, monolinoleoyl glycerol and monooleoyl glycerol.

27. The composition of claim 19 wherein said copolymer comprises the reaction product of said monoglyceride, polybasic acid or derivative thereof, N-methyl diethanolamine, and 3-dimethylamino-1,2 propanediol.

28. The composition of claim 19 wherein said bioactive agent is selected from the group consisting of antiinfectives, analgesics, anorexics, antihelmintics, antiarthritics, antiasthmatics, anticonvulsants, antidepressants, antidiuretics, antidiarrheals, antihistamines, antiinflammatory agents, antimigraine preparations, antinauseants, antineoplastics, antiparkinsonism drugs, antipruritics, antipsychotics, antipyretics, antispasmodics, anticholinergics, sympathomimetics, xanthine derivatives, calcium channel blockers, beta-blockers, antiarrhythmics, antihypertensives, diuretics, vasodilators, central nervous system stimulants, decongestants, hormones, steroids, hypnotics, immunosuppressives, muscle relaxants, parasympatholytics, psychostimulants, sedatives, tranquilizers, naturally derived or genetically engineered proteins, growth factors, polysaccharides, glycoproteins, or lipoproteins, oligonucleotides, antibodies, antigens, cholinergics, chemotherapeutics, hemostatics, clot dissolving agents, radioactive agents and cystostatics.

29. The composition of claim 19 further comprising an aliphatic polyester prepared from the group of monomers selected from the group consisting of glycolide, L-lactide, D-lactide, meso-lactide, rac-lactide, ε-caprolactone, trimethylene carbonate, p-dioxanone, 1,4-dioxanone, 1,4-dioxepan-2-one, 1,5-dioxepan-2-one and substituted derivatives thereof.

30. The composition of claim 19 wherein said polymer is a polymeric wax having a melting point between about 25° C. and about 70° C.

31. The composition of claim 19 wherein said polymer is a liquid polymer having a melting point below about 25° C.

32. A microdispersion comprising: a blend of a polymeric wax and a liquid polymer, wherein said polymeric wax and said liquid polymer comprise the reaction product of a polybasic acid or derivative thereof, a monoglyceride, and a cationic polyol.

33. The microdispersion of claim 32 wherein said polybasic acid or derivative thereof is selected from the group consisting of succinic acid, succinic anhydride, malic acid, tantaric acid, citric acid, diglycolic acid, diglycolic anhydride, glutaric acid, glutaric anhydride, adipic acid, pimelic acid, suberic acid, sebacic acid, fumaric acid, maleic acid, maleic anhydride, mixed anhydrides, esters, activated esters and acid halides.

34. The microdispersion of claim 32 wherein said monoglyceride is selected from the group consisting of monostearoyl glycerol, monopalmitoyl glycerol, monomyrisitoyl glycerol, monocaproyl glycerol, monodecanoyl glycerol, monolauroyl glycerol, monolinoleoyl glycerol and monooleoyl glycerol.

35. The microdispersion of claim 34 wherein said polybasic acid derivative is succinic anhydride.

36. The microdispersion of claim 34 wherein said polybasic acid is succinic acid.

37. The microdispersion of claim 34 wherein said cationic is selected from the group consisting of N-methyl diethanolamine, and 3-dimethylamino-1,2 propanediol.

38. The microdispersion of claim 32 further comprising an effective amount of a bioactive agent.

* * * * *